United States Patent
Zhan et al.

(10) Patent No.: US 9,783,461 B2
(45) Date of Patent: Oct. 10, 2017

(54) OLEFIN OLIGOMERIZATION USING DELAMINATED ZEOLITE SUPPORTS AS CATALYST

(71) Applicant: Chevron U.S.A. Inc., San Ramon, CA (US)

(72) Inventors: Bi-Zeng Zhan, Albany, CA (US); Stacey Ian Zones, San Francisco, CA (US); Christopher M. Lew, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/919,591

(22) Filed: Oct. 21, 2015

(65) Prior Publication Data

US 2016/0122258 A1    May 5, 2016

Related U.S. Application Data

(60) Provisional application No. 62/075,017, filed on Nov. 4, 2014.

(51) Int. Cl.
| | |
|---|---|
| C07C 2/04 | (2006.01) |
| C07C 2/12 | (2006.01) |
| C07C 2/24 | (2006.01) |
| C10G 50/00 | (2006.01) |
| B01J 37/34 | (2006.01) |
| B01J 29/70 | (2006.01) |
| B01J 29/74 | (2006.01) |
| B01J 29/86 | (2006.01) |
| B01J 35/00 | (2006.01) |
| B01J 35/10 | (2006.01) |
| B01J 38/10 | (2006.01) |
| B01J 29/90 | (2006.01) |

(52) U.S. Cl.
CPC ............... *C07C 2/12* (2013.01); *B01J 29/70* (2013.01); *B01J 29/74* (2013.01); *B01J 29/86* (2013.01); *B01J 35/002* (2013.01); *B01J 35/1019* (2013.01); *B01J 35/1042* (2013.01); *B01J 35/1057* (2013.01); *B01J 35/1061* (2013.01); *B01J 37/343* (2013.01); *C10G 50/00* (2013.01); *B01J 29/90* (2013.01); *B01J 38/10* (2013.01); *B01J 2229/186* (2013.01); *B01J 2229/22* (2013.01); *B01J 2229/34* (2013.01); *B01J 2229/37* (2013.01); *B01J 2229/42* (2013.01); *C07C 2529/70* (2013.01); *C07C 2529/74* (2013.01)

(58) Field of Classification Search
CPC .. C07C 2/12; C07C 2/24; B01J 37/343; B01J 35/1019; B01J 35/1042; B01J 29/86; B01J 29/74; B01J 29/70; B01J 35/1057; B01J 35/002; B01J 35/1061; B01J 2229/186; B01J 2229/22; B01J 38/10; B01J 29/90; B01J 2229/37; B01J 2229/42; B01J 2229/34; C10G 50/00
See application file for complete search history.

(56) References Cited

U.S. PATENT DOCUMENTS

| | | | |
|---|---|---|---|
| 4,921,594 A | 5/1990 | Miller | |
| 5,316,753 A | 5/1994 | Nakagawa | |
| 7,108,843 B2 | 9/2006 | Zones et al. | |
| 7,550,073 B2 * | 6/2009 | Zones | B01J 29/86 |
| | | | 208/113 |
| 8,637,419 B2 | 1/2014 | Zhan | |
| 2006/0138025 A1 | 6/2006 | Zones et al. | |
| 2012/0148487 A1* | 6/2012 | Katz | C01B 39/026 |
| | | | 423/718 |
| 2016/0115396 A1 | 4/2016 | Zhan | |
| 2016/0115397 A1 | 4/2016 | Zhan | |
| 2016/0122260 A1 | 5/2016 | Zhan et al. | |

OTHER PUBLICATIONS

Archer, et al. "Physiochemical Properties and Catalytic Behavior of the Molecular Sieve SSZ-70", Chemistry of Materials, 2010, vol. 22, pp. 2563-2572.
Runnebaum R.C., et al., "Role of Delamination in Zeolite-Catalyzed Aromatic Alkylation: UCB-3 versus 3-D AI-SSZ-70", ACS Catalysis, vol. 4, No. 7, pp. 2364-2368 (2014).
Corma, A. et al., "Delaminated zeolite precursors as selective acidic catalysts", Nature, vol. 396, Nov. 1998, pp. 353-356.
Ogino, et al., "Heteroatom-Tolerant Delamination of Layered Zeolite Precursor Materials", Chemistry of Materials, vol. 25, No. 9, pp. 1502-1509 (2013).

* cited by examiner

*Primary Examiner* — In Suk Bullock
*Assistant Examiner* — Jason Chong
(74) *Attorney, Agent, or Firm* — E. Joseph Gess; Melissa M. Hayworth; Mark L. Warzel

(57) ABSTRACT

Provided is an improved process for olefin oligomerization allowing one to realize superior selectivity. The process comprises contacting a hydrocarbon feed comprised of straight and branched chain olefins under oligomerization conditions with a catalyst comprising delaminated SSZ-70. The delaminated SSZ-70 offers a zeolite layer with a single unit cell of thickness in one dimension, allowing for elimination of mass transfer in comparison with regular SSZ-70. The result is superior selectivity.

10 Claims, 1 Drawing Sheet

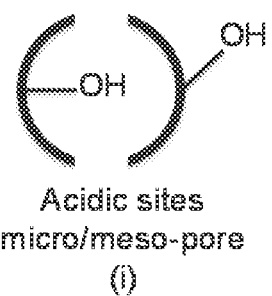 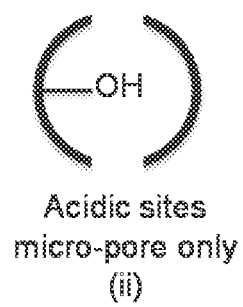 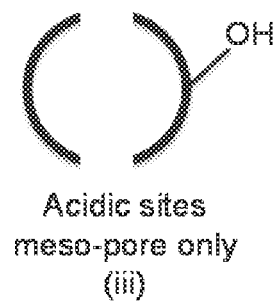
Acidic sites micro/meso-pore (i)    Acidic sites micro-pore only (ii)    Acidic sites meso-pore only (iii)

OLEFIN OLIGOMERIZATION USING DELAMINATED ZEOLITE SUPPORTS AS CATALYST

CROSS REFERENCE TO RELATED APPLICATION

This application claims priority to U.S. Provisional No. 62/075,017, filed Nov. 4, 2014, entitled "Olefin Oligomerization Using Delaminated Zeolite Supports as Catalysts", the contents of which are herein incorporated by reference in their entirety.

FIELD OF THE INVENTION

The present invention relates to delaminated zeolites and their use as catalysts in the hydroprocessing of hydrocarbons. More specifically, the present invention relates to the use of delaminated SSZ-70 as a catalyst in liquid olefin oligomerization.

BACKGROUND

Zeolites are widely used as acidic catalysts for refining applications attributed to their unique and uniform pore structure with sizes in the sub-nanometer range. The pore sizes of zeolites dictate reaction of refining processes including hydroisomerization, hydrocracking, olefin alkylation and olefin oligomerization, thus dictate reaction selectivity. However, hydroprocessing products often experience varying degree of continuously (over)cracking when they diffuse out of nanometer-scaled zeolitic channels. Thus elimination of these types of side-reactions is significant for efficiency improvement. One of the solutions for preventing overcracking is reduction of acidic strength. But this approach reduces catalyst activity at the same time.

A. Corma et al. in "Delaminated zeolite precursors as selective acidic catalysts", *Nature*, vol. 396, November 1998, pp 353-356, discusses delaminating MCM-22(P), the precursor of both MCM-22 and ERB-1 zeolites. The delaminated zeolite is designated ITQ-2, and was shown to have catalytic potential.

Molecular sieve SSZ-70 is known and is discussed in "Physiochemical Properties and Catalytic Behavior of the Molecular Sieve SSZ-70", Archer et al. *Chemistry of Materials*, 2010, vol. 22, pp 2563-2572. A method for the synthesis of the SSZ-70 is discussed. Pure silica, borosilicate and aluminosilicate SSZ-70 materials were prepared and characterized. The catalytic activity of Al-SSZ-70 materials was tested using the CI (Constraint Index) test. U.S. Pat. Nos. 7,108,843 and 7,550,073 also discuss the synthesis of the molecular sieve SSZ-70, and its use in hydrocarbon conversion processes such as hydrocracking. The disclosure of both U.S. Pat. Nos. 7,108,843 and 7,550,073 are expressly incorporated herein by reference in their entirety.

It would be of great value to the hydroprocessing industry if a more effective and selective olefin oligomerization process were discovered.

SUMMARY

Provided is a process involving the oligomerization of liquid olefins in the presence of a delaminated SSZ-70 catalyst. The delaminated SSZ-70 has been found to provide unexpected improvements in the catalysis of hydroprocessing hydrocarbons. It has been found that delaminated SSZ-70 offers a zeolite layer with a single unit cell of thickness in one dimension, allowing an elimination of mass transfer in comparison with regular SSZ-70 (non-delaminated). It also provides the possibility of eliminating the spatial constraint on oligomerized product to meet some specific applications. For example, significant improvement of selectivity to larger molecules with boiling point in the range of base oil (e.g. 600° F.+) is believed possible in olefin oligomerization when using a delaminated SSZ-70 catalyst with acidic sites located on the external surface compared to regular SSZ-70.

Among other factors, it has been discovered that using a catalyst comprising delaminated SSZ-70 as a catalyst in an olefin oligomerization process, particularly liquid olefin oligomerization, superior selectivity can be realized. A more effective process for preparing base oils is achieved, as significant improvement of selectivity to larger molecules with a boiling point in the 600° F.+ range is possible.

BRIEF DESCRIPTION OF THE DRAWING

The FIGURE schematically depicts acid sites on delaminated SSZ-70. It shows possibility of preparation of SSZ-70-based catalysts having varying location of acidic sites (i) zeolitic acidic sites on both external and internal surface, (ii) zeolitic acidic sites on internal surface only, (iii) zeolitic acidic sites on external surface only.

DETAILED DESCRIPTION OF THE PREFERRED EMBODIMENTS

The present invention relates to an improved olefin oligomerization process which allows one to achieve superior selectivity. The process comprises contacting a hydrocarbon feed comprised of straight and branched chain olefins under oligomerization conditions with a catalyst comprising delaminated SSZ-70. It has been found that delaminated SSZ-70 offers a zeolite layer with a single unit cell of thickness in one dimension, allowing for elimination of mass transfer in comparison with regular SSZ-70. The result is superior selectivity.

The delaminated SSZ-70 also exhibits features of maintaining zeolitic acidic strength and spatial constraint of the internal zeolitic framework. This provides one with the opportunity of controlling novel chemistry by tailoring the location of acidic sites. Turning to the FIGURE, three scenarios are schematically provided of controlled location of acidic sites that can be prepared with starting materials of delaminated SSZ-70 in either the Al- or B-form.

The molecular sieve SSZ-70 is known, as is synthesis thereof. U.S. Pat. No. 7,108,843, issued Sep. 19, 2006, for example describes the molecular sieve SSZ-70 and a synthesis for preparing the molecular sieve. The SSZ-70 is characterized in U.S. Pat. No. 7,108,843 by its X-ray diffraction pattern before calcination, and by its X-ray diffraction pattern after calcination. The disclosure of U.S. Pat. No. 7,108,843 is hereby expressly incorporated by reference herein in its entirety.

The delaminated SSZ-70 can be obtained by delaminating the SSZ-70 molecular sieve using conventional techniques of delamination. In one embodiment, the techniques described in U.S. 2012/0148487, published Jun. 14, 2012, would be quite effective, which publication is expressly incorporated herein by reference in their entirety.

In general, an aqueous mixture of chloride and fluoride anions, e.g., alkylammoniumhalides and the SSZ-70 is prepared. The aqueous mixture is maintained at a pH less than 12, e.g., about 9, and maintained at a temperature in the range of 5-150° C. for a length of time sufficient to effect the desired delamination. The oxide product is then recovered, e.g., by acidification to a pH of about 2 followed by centrifugation.

In one embodiment, a non-aqueous mixture of chloride and fluoride anions, i.e., a mixture comprising an organic solvent, is maintained at a temperature in the range of from 5-150° C. to effect the desired delamination. The organic solvent can be any suitable organic solvent which swells the starting material such as dimethyl formamide (DMF). The delaminated product can then be recovered from the mixture. Generally, acidification is used to recover the product. Sonication prior to recovery need not be employed, but sonification can be employed in the process if desired.

The chloride and fluoride anions can be obtained from any source of the anions. Any compound which will provide the anions in aqueous solution can be used. The cation is generally not important. Providing the fluoride and chloride anions is important. Bromide anions can also be present, but both fluoride and chloride anions must be present. The cations can be any cation, with the use of alkylammonium cations being suitable in one embodiment. The alkyl group of such a cation can be any length, and in one embodiment ranges from 1-20 carbons. Tetrabutylammonium cations in particular have been found useful. The molar ratio of chloride to fluoride anions can be 100 or less, generally from 100:1 to 1:100. In one embodiment, the ratio can range from 50:1 to 1:50. It is the combination of the fluoride and chloride anions which has been discovered to be important.

The pH used in the synthesis when an aqueous mixture is used is lower than that generally used in delamination synthesis. The pH is generally 12 or less, but can be any pH which does not transform the silica in the zeolite to create an amorphous silica phase. A pH of 12 or less generally accomplishes this task and thereby allows one to obtain a delaminated layered zeolite precursor material substantially without an amorphous phase. In another embodiment, the pH is 11 or less, and even 10 or less, with a pH of about 9 or less also being quite advantageous. A pH of approximately 9 is typically used in fluoride-mediated synthesis of zeolites.

The temperature used in the process for either the aqueous or non-aqueous mixture can range widely. In general a temperature for the aqueous solution of from 5-150° C. is suitable. In another embodiment, the temperature can range from 50-100° C.

The length of time the zeolite is allowed to swell, and delaminate, in the aqueous solution can vary greatly. Generally, the time can vary from 30 minutes to one month. In one embodiment, the time ranges from 2 hours to 50 hours. In another embodiment, the time can range from 5 to 20 hours prior to collection of the product.

The delaminated oxide product is collected using conventional techniques such as centrifugation. An acid treatment step can be employed prior to centrifugation, and may be conveniently conducted by contacting the swollen or partially delaminated layered zeolite precursor material with a strong acid, e.g., a mineral acid such as hydrochloric acid or nitric acid, at low pH, e.g., pH 2. Collection of the resulting oxide material product can be performed by centrifugation.

The delaminated SSZ-70 can be used to oligomerize straight and branched chain olefins having from about 2 to 21 and preferably 2-5 carbon atoms. The oligomers which are the products of the process are medium to heavy olefins which are useful for fuels and lube oil. It can also useful as feedstocks for chemicals and surfactants.

The oligomerization process comprises contacting the olefin feedstock in the liquid phase with a catalyst comprising the delaminated SSZ-70. The catalyst can comprise pure delaminated SSZ-70 or in mixture with any suitable conventional catalyst, and can be present in the catalyst in an amount as small as 2 parts by weight. Generally, the catalyst will comprise at least 2 parts by weight of the delaminated SSZ-70. The delaminated SSZ-70 can be in the hydrogen form. The delaminated SSZ-70 can be a delaminated Al-SSZ-70 material or a delaminated B-SSZ-70 material.

The delaminated SSZ-70 catalyst can contain transition metals, which are introduced through any conventional methods such as impregnation or ion exchange with their corresponding metal salts or oxides. In one embodiment, the delaminated SSZ-70 catalyst comprises a noble metal selected from the group of nickel (Ni), palladium (Pd), platinum (Pt), ruthenium (Ru), rhodium (Rh), iron (Fe), gold (Au), silver (Ag) and mixtures thereof. In another embodiment, the delaminated SSZ-70 catalyst contains at least one metal selected from Groups VI through VIII of the Period Table.

The deactivated catalyst can be regenerated by hydrogenation or hydrocracking of coke or heavy hydrocarbons deposited on its surface under hydrogenation and hydrocracking reaction conditions.

In one embodiment, the delaminated SSZ-70 can be used to oligomerize olefin feeds comprising olefins containing from 2 to 8 carbon atoms, preferably the olefin feeds are alpha-olefins, especially linear alpha-olefins. Ethylene is especially preferred but other suitable olefins include, but are not limited to, propylene, 1-butene, 1-pentene, 1-hexene, 1-octene, and mixtures thereof. The olefin feed can be a mixture of olefins or a single olefin such as ethylene.

The delaminated SSZ-70 catalyst can be contacted with the olefin feed in any convenient manner. Sometimes a suitable solvent, such as paraffins or aromatics, can be added to co-process with olefin feeds.

The oligomerization process can be conducted as a batch, continuous, semi-bath or multi-step process. It can be conducted in fixed-bed reactor process with up and down flow. Inert gas or refinery light hydrocarbon gas stream can be added to the process. The process can be conducted using suitable equipment in the art.

The reaction conditions for oligomerizing the olefin feed can vary broadly, depending on the desired product, and the olefins employed. They include the temperature and pressure sufficient to produce the desired oligomerized product. Generally, the reaction temperatures will be in the range of from 0° C. to 500° C., preferably from 25° C. to 400° C., and more preferably from 50° C. to 350° C. Generally, the pressure is at least 200 psi, preferably the pressure is greater than 500 psi.

The olefin product generally comprises a mixture of alpha-olefins containing from 4 to 54 carbon atoms, preferably from 8 to 50. The olefin product contains only trace amounts of vinylidene, branched and isomerized olefins. When proper conditions and catalyst are employed, the olefin product contains less than 1000 ppm polymerized olefin.

A typical product distribution for the process is shown below. The product distribution is due to a geometric product distribution [see *Alpha Olefin Handbook* by Lappin et al., page 28].

$C_4$ to $C_8$ content=34%.
$C_{10}$ to $C_{16}$ weight content=25%.
$C_{18}$ to $C_{54}$ weight content=33%.

The olefin products of this invention have established utility in a wide variety of applications such as, for example, fuels, lube oils, surfactants and monomers for use in the preparation of polymers.

Due to the use of the delaminated SSZ-70 catalyst of the present invention, greater selectivity of the product can be achieved. Tailoring the product obtained to a specific application is therefore possible by using the delaminated SSZ-70 catalyst.

The following examples are provided to further illustrate the present invention, and are not meant to be limiting.

EXAMPLES

Preparation of Al-SSZ-70

7.67 g aluminum hydroxide (Reheis F-2000) was added to 395.55 g NaOH (1M) in a 1 gallon liner. 240 g Cabosil fumed silica was slowly added while stirring. At the same time, 1707.47 g 1,3-diisobutylimidazolium hydroxide (9 wt %, SDAOH-1) and 149.27 g deionized water was added to the liner. The final molar composition was 1 $SiO_2$:0.01 $Al_2O_3$:0.2 SDAOH-1:0.1 NaOH:30$H_2O$. The liner was placed into a 1 gallon, overhead stirred autoclave. The temperature was increased to 160° C. with a ramp time of 8 h and a stir rate of 150 rpm. The reaction mixture was synthesized for 120 h. The final solids were filtered and washed with deionized water to a conductivity of <50 μS/cm.

Preparation of B-SSZ-70

2.91 g $H_3BO_3$ was added to 84.20 g NaOH (1M) in a 1 L Teflon liner. 50.52 g of Cabosil fumed silica was slowly added while stirring. At the same time, 413.6 g 1,3-Bis(cyclohexyl)imidazolium hydroxide (0.40 M, SDAOH-2) was added to the liner. The final molar composition was 1 $SiO_2$:0.03$B_2O_3$:0.2 SDAOH-2:0.1 NaOH:30$H_2O$. The liner was placed into a 1 L, overhead stirred, Parr autoclave. The temperature was increased to 160° C. with a ramp time of 8 h and a stir rate of 70 rpm. The reaction mixture was synthesized for 116 h. The final solids were filtered and washed with deionized water to a conductivity of 26 μS/cm.

Preparation of Delaminated B-SSZ-70

5 g of as-made B-SSZ-70 was added to a 500 mL, 1-neck, round-bottom flask. 200 mL N,N-dimethylformamide, 5.5 g cetyltrimethylammonium bromide, 8.5 g tetrabutylammonium fluoride trihydrate, and 8.5 g tetrabutylammonium chloride were added to the flask. The contents of the flask were stirred in a 95° C. oil bath for 48 h. The contents of the flask were then poured into a 500 mL wide-mouth bottle and sonicated in an ice bath for 2 h using a sonicator made by Sonics and Materials Inc. (Vibracell VC 750, 35% power) operating under pulse mode (4 s on and 1 s off). The delaminated solution was divided into four equal parts and poured into four 250 mL centrifuge bottles. 200 mL tetrahydrofuran was added to each centrifuge bottle, and the bottles were centrifuged at 8500 rpm (11000 g) for 10 min. The solution was decanted, 250 mL fresh THF was added to each bottle, and the solids were redispersed into the solution. The bottles were centrifuged and decanted. 250 mL diethyl ether was added to each bottle and the solids were redispersed into the solution. The bottles were centrifuged, decanted, and the solids were dried at 80° C. The sample was calcined at 550° C. for six hours at a ramp rate of 1° C./min in flowing air.

Preparation of Al-Exchanged Delaminated Al-SSZ-70

3 g of delaminated B-SSZ-70 was added to a 250 mL, 1-neck, round-bottom flask. 75 g deionized water and 11.25 g aluminum nitrate nonahydrate were added to the flask. The contents of the flask were stirred in a 95° C. oil bath for 96 h. The mixture was filtered and washed with 300 mL HCl (pH=2). The mixture was filtered and washed with another 300 mL HCl. The mixture was filtered and washed with deionized water to a pH of 7. The solids were dried at 80° C.

Preparation of a Catalyst Base Containing 10% Al-SSZ-70 (Catalyst Base-A, Base Case)

A comparative catalyst was prepared per the following procedure: 90 parts by weight pseudo boehmite alumina powder (obtained from Sasol), and 10 parts by weight of Al-SSZ-70 zeolite were mixed well. The SSZ-70 zeolite employed had the following properties: a $SiO_2/Al_2O_3$ mole ratio of about 80. A diluted $HNO_3$ acid aqueous solution (1 wt. %) was added to the mix powder to form an extrudable paste. The paste was extruded in 1/16 inch asymmetric quadrilobe shape, and dried at 250° F. (121° C.) overnight. The dried extrudates were calcined at 850° F. (454° C.) for 1 hour with purging excess dry air and cooled down to room temperature.

Preparation of 0.5 wt % Pt Catalyst Containing 10% Al-SSZ-70 (Catalyst-A, Base Case)

Impregnation of Pt metal was done using an aqueous solution containing 3.3% Pt salt in concentrations equal to the target metal loadings of 0.5 wt. % Pt based on the bulk dry weight of the finished catalyst. The total volume of the solution matched the 103% water pore volume of the above calcined base extrudate sample (incipient wetness method). The metal solution was added to the base extrudates of base-A (base case) gradually while tumbling the extrudates. When the solution addition was completed, the soaked extrudates were aged for 2 hours. Then the extrudates were dried at 250° F. (121° C.) overnight. The dried extrudates were calcined at 662° F. (350° C.) for 1 hour with purging excess dry air, and cooled down to room temperature. The performance of this catalyst was evaluated with nC16 pure compound.

Preparation of a New Catalyst Base Containing 10% Delaminated Al-SSZ-70 (Catalyst Base-B)

A new isomerization-improved catalyst base was prepared per the following procedure: 90 parts by weight pseudo boehmite alumina powder (obtained from Sasol), and 10 parts by weight of delaminated Al-SSZ-70 zeolite were mixed well. A diluted $HNO_3$ acid aqueous solution (1 wt. %) was added to the mix powder to form an extrudable paste. The paste was extruded in 1/16 inch asymmetric quadrilobe shape, and dried at 250° F. (121° C.) overnight. The dried extrudates were calcined at 850° F. (454° C.) for 1 hour with purging excess dry air and cooled down to room temperature.

Preparation of 0.5 wt % Pt Catalyst Containing 10% Delaminated Al-SSZ-70 (Catalyst-B)

Impregnation of Pt was done using an aqueous solution containing 3.3 wt. % Pt salt in concentrations equal to the target metal loadings of 0.5 wt. % Pt based on the bulk dry weight of the finished catalyst. The total volume of the solution matched the 103% water pore volume of the above calcined base extrudate sample (incipient wetness method). The metal solution was added to the base extrudates of base-B gradually while tumbling the extrudates. When the solution addition was completed, the soaked extrudates were aged for 2 hours. Then the extrudates were dried at 250° F. (121° C.) overnight. The dried extrudates were calcined at 662° F. (350° C.) for 1 hour with purging excess dry air, and cooled down to room temperature. The performance of this catalyst was evaluated with nC16 pure compound.

Preparation of a Catalyst New Base Containing 2% Delaminated Al-SSZ-70 (Catalyst Base-C)

A new isomerization-improved catalyst base was prepared per the following procedure: 25 parts by weight pseudo boehmite alumina powder (obtained from Sasol), 73 parts by weight of silica-alumina powder (obtained from Sasol), and 2 parts by weight of delaminated Al-SSZ-70 zeolite were mixed well. A diluted $HNO_3$ acid aqueous solution (1 wt. %) was added to the mix powder to form an extrudable paste. The paste was extruded in 1/16 inch asymmetric quadrilobe shape, and dried at 250° F. (121° C.) overnight. The dried extrudates were calcined at 850° F. (454° C.) for 1 hour with purging excess dry air and cooled down to room temperature.

Preparation of 0.5 wt % Pt Catalyst Containing 2% Delaminated Al-SSZ-70 (Catalyst-C)

Impregnation of Pt was done using an aqueous solution containing 3.3 wt. % Pt salt in concentrations equal to the target metal loadings of 0.5 wt. % Pt based on the bulk dry weight of the finished catalyst. The total volume of the solution matched the 103% water pore volume of the above calcined base extrudate sample (incipient wetness method). The metal solution was added to the base extrudates of base-C gradually while tumbling the extrudates. When the solution addition was completed, the soaked extrudates were aged for 2 hours. Then the extrudates were dried at 250° F. (121° C.) overnight. The dried extrudates were calcined at 662° F. (350° C.) for 1 hour with purging excess dry air, and cooled down to room temperature. The performance of this catalyst was evaluated with nC16 pure compound.

Preparation of a New Catalyst Base Containing 3% Delaminated B-SSZ-70 (Catalyst Base-D)

A new isomerization-improved catalyst base was prepared per the following procedure: 25 parts by weight pseudo boehmite alumina powder (obtained from Sasol), 72 parts by weight of silica-alumina powder (obtained from Sasol), and 3 parts by weight of delaminated B-SSZ-70 zeolite were mixed well. A diluted $HNO_3$ acid aqueous solution (1 wt. %) was added to the mix powder to form an extrudable paste. The paste was extruded in 1/16 inch asymmetric quadrilobe shape, and dried at 250° F. (121° C.) overnight. The dried extrudates were calcined at 850° F. (454° C.) for 1 hour with purging excess dry air and cooled down to room temperature.

Preparation of 0.5 wt % Pt Catalyst Containing 3% Delaminated B-SSZ-70 (Catalyst-D)

Impregnation of Pt was done using an aqueous solution containing 3.3 wt. % Pt salt in concentrations equal to the target metal loadings of 0.5 wt. % Pt based on the bulk dry weight of the finished catalyst. The total volume of the solution matched the 103% water pore volume of the above calcined base extrudate of base-D (incipient wetness method). The metal solution was added to the base extrudates gradually while tumbling the extrudates. When the solution addition was completed, the soaked extrudates were aged for 2 hours. Then the extrudates were dried at 250° F. (121° C.) overnight. The dried extrudates were calcined at 662° F. (350° C.) for 1 hour with purging excess dry air, and cooled down to room temperature.

All the catalysts and their supports were characterized as follows:

Brönsted acidity: determined by isopropylamine-temperature-programmed desorption (IPam TPD) adapted from the published descriptions by T. J. Gricus Kofke, R. K. Gorte, W. E. Farneth, J. Catal. 114, 34-45, 1988; T. J. Gricus Kifke, R. J. Gorte, G. T. Kokotailo, J. Catal. 115, 265-272, 1989; J. G. Tittensor, R. J. Gorte and D. M. Chapman, J. Catal. 138, 714-720, 1992. Samples are pre-treated at 400-500° C. for 1 hour in flowing dry $H_2$. The dehydrated samples are then cooled down to 120° C. in flowing dry He and held at 120° C. for 30 minutes in a flowing He saturated with isopropylamine for adsorption. The isopropylamine-saturated samples are then heated up to 500° C. at a rate of 10° C./min in flowing dry He. The Brönsted acidity is calculated based on the weight loss vs. temperature by TGA and effluent $NH_3$ and propene by Mass Spectrometer.

Surface area: determined by $N_2$ adsorption at its boiling temperature. BET surface area is calculated by the 5-point method at $P/P_0$=0.050, 0.088, 0.125, 0.163, and 0.200. Samples are first pre-treated at 400° C. for 6 hours in the presence of flowing, dry $N_2$ so as to eliminate any adsorbed volatiles like water or organics.

TABLE 1

Properties of calcined catalyst bases containing Al-SSZ-70 and delaminated Al-SSZ-70

| Catalyst base | Zeolite | Micropore volume, cc/g | Ext. SA, m2/g | Brönsted acidity, µmol/g |
| --- | --- | --- | --- | --- |
| Base-A (base case) | Original SSZ-70 (w/o delaminated) | 0.0214 | 207 | 161 |
| Base-B | Delaminated SSZ-70 | 0.0068 | 277 | 131 |

The high external surface area of the support of the new catalyst base-B in comparison with the base case catalyst support of catalyst base-A is contributed to the high external surface area of delaminated Al-SSZ-70. In contrast to the base case catalyst base-A, the delaminated SSZ-70-containing catalyst base-B showed a lower micropore volume. Delaminated SSZ-70 showed less Brönsted acidic density than its original precursor.

TABLE 2

Properties of calcined catalyst bases containing delaminated Al-SSZ-70 and delaminated B-SSZ-70

| Catalyst base | Zeolite | Surface Area, m2/g | Pore volume, cm3/g | Mesopore size, nm | Brönsted acidity, µmol/g |
| --- | --- | --- | --- | --- | --- |
| Base-C | 2% Delaminated Al-SSZ-70 | 421 | 0.81 | 11.3 | 142 |
| Base-D | 3% Delaminated B-SSZ-70 | 420 | 0.80 | 11.2 | 158 |

The high Brönsted acidity of the catalyst base-D suggests Al exchanged to the B site of zeolite framework during the extrusion process. Thus, it is concluded that the Al exchange process can be eliminated in the preparation of hydroprocessing catalysts using delaminated B-SSZ-70 zeolite.

It is expected that if the delaminated SSZ-70, whether in the delaminated Al-SSZ-70 or B-SSZ-70 form, was used in an olefin oligomerization reaction, exceptional conversion and selectivity would be observed.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. An oligomerization process comprising reacting an olefin feed comprising at least one olefin having from 2 to 21 carbon atoms under oligomerization conditions with a catalyst comprising delaminated SSZ-70 having a layer with a single unit cell of thickness in one dimension.

2. The process of claim 1, wherein the olefin feed comprises straight and branched chain olefins.

3. The process of claim 1, wherein the olefin feed comprises ethylene.

4. The process of claim 1, wherein the oligomerization conditions include a temperature in a range of from 0° C. to 500° C.

5. The process of claim 1, wherein the catalyst further comprises at least one transition metal.

6. The process of claim 5, wherein the catalyst comprises at least one Group VIII metal.

7. The process of claim 1, wherein the delaminated SSZ-70 is a delaminated Al-SSZ-70 material.

8. The process of claim 1, wherein the delaminated SSZ-70 is a delaminated B-SSZ-70 material.

9. The process of claim 1, wherein a product comprising a mixture of alpha-olefins containing from 4 to 54 carbon atoms is recovered.

10. The process of claim 1, wherein the reaction is conducted in the liquid phase.

* * * * *